United States Patent
Cao et al.

(10) Patent No.: US 11,939,625 B2
(45) Date of Patent: Mar. 26, 2024

(54) METHOD AND SENSOR FOR DETECTING L-CYSTINE

(71) Applicant: CHANGSHA UNIVERSITY OF SCIENCE AND TECHNOLOGY, Changsha (CN)

(72) Inventors: Zhong Cao, Changsha (CN); Jia Yang, Changsha (CN); Chen Liu, Changsha (CN); Zhongliang Xiao, Changsha (CN); Dan Li, Changsha (CN); Ling Zhang, Changsha (CN); Yuyang Zhang, Changsha (CN); Jiaxin Li, Changsha (CN)

(73) Assignee: CHANGSHA UNIVERSITY OF SCIENCE AND TECHNOLOGY, Changsha (CN)

( * ) Notice: Subject to any disclaimer, the term of this patent is extended or adjusted under 35 U.S.C. 154(b) by 621 days.

(21) Appl. No.: 17/258,932

(22) PCT Filed: Aug. 24, 2019

(86) PCT No.: PCT/CN2019/102372
§ 371 (c)(1),
(2) Date: Jan. 8, 2021

(87) PCT Pub. No.: WO2020/043026
PCT Pub. Date: Mar. 5, 2020

(65) Prior Publication Data
US 2021/0123093 A1    Apr. 29, 2021

(30) Foreign Application Priority Data
Aug. 28, 2018   (CN) .......................... 201810984084.5
Aug. 28, 2018   (CN) .......................... 201821387669.0

(51) Int. Cl.
*C12Q 1/6809*   (2018.01)
*G01N 27/26*    (2006.01)

(52) U.S. Cl.
CPC ........... *C12Q 1/6809* (2013.01); *G01N 27/26* (2013.01); *C12Q 2500/00* (2013.01); *C12Q 2545/10* (2013.01); *C12Q 2560/00* (2013.01); *C12Q 2565/607* (2013.01)

(58) Field of Classification Search
CPC ............. C12Q 1/6809; C12Q 2500/00; C12Q 2545/10; C12Q 2560/00; C12Q 2565/607; G01N 27/26; G01N 33/54373; G01N 27/4145
See application file for complete search history.

(56) References Cited

FOREIGN PATENT DOCUMENTS

| CN | 102288657 A | 12/2011 |
| CN | 102645476 A | 8/2012 |
| CN | 105334248 A | 2/2016 |
| CN | 105891296 A | 8/2016 |
| CN | 107976476 A | 5/2018 |
| CN | 109115856 A | 1/2019 |
| CN | 208860792 U | 5/2019 |
| WO | 2007145343 A1 | 12/2007 |

OTHER PUBLICATIONS

Nishitani et al. Three-Dimensional Polymeric Biointerface for Ultra-Sensitive and Selective Detection of Low-Molecular-Weight Biomarker Using Semiconductor-Based Biosensor, 2018, 85(9), 9-14. (Year: 2018).*
Jia Yang et al., L-Cystine Sensor Based on Modification of Extended Gate of FET with Polydithiodipropanesulfonic Acid Membrane, Chemical Journal of Chinese Universities, 2018, pp. 2386-2394, vol. 39, No. 11.

* cited by examiner

*Primary Examiner* — Narayan K Bhat
(74) *Attorney, Agent, or Firm* — Bayramoglu Law Offices LLC

(57) ABSTRACT

A method and a sensor for detecting L-cystine are disclosed. The method is implemented by assembling a sodium 3,3'-dithiodipropane sulfonate (SPS) membrane on a surface of Au membrane layer of an Au electrode and using an extended gate of field effect transistor (FET) and in-situ signal amplification of the FET to detect L-cystine sensitively. The polyanion of the SPS membrane adsorbs and binds a positively charged target L-cystine through electrostatic interaction, thus forming an electric double layer structure to generate a membrane potential identifying a monovalent organic ammonium ion. The sensor includes the FET, wherein a gate-extended gold electrode is arranged on the FET, and the SPS membrane is assembled on the surface of the Au membrane layer of the gate-extended gold electrode. The sensor has an excellent Nernst response to L-cystine.

12 Claims, 5 Drawing Sheets

METHOD AND SENSOR FOR DETECTING L-CYSTINE

CROSS REFERENCE TO THE RELATED APPLICATIONS

This application is the national phase entry of International Application No. PCT/CN2019/102372, filed on Aug. 24, 2019, which is based upon and claims priority to Chinese Patent Applications No. 201810984084.5 and No. 201821387669.0, filed on Aug. 28, 2018, the entire contents of which are incorporated herein by reference.

TECHNICAL FIELD

The present invention relates to the technical field of chemical/biological sensing, and specifically relates to a method and a sensor for detecting L-cystine based on an ion-selective membrane potential, which is suitable for online detection in healthy breeding and life sciences.

BACKGROUND

L-cystine is a sulfur-containing amino acid mostly found in keratin of the nails and hair. In addition of body proteins, it is also widely found in living cells and tissues of organisms, exemplifying a variety of important physiological functions. For example, L-cystine can promote oxidation and reduction in body cells and leukocyte proliferation, invigorate liver functions, neutralize toxins, prevent development of pathogenic bacteria and maintain protein configuration. Sulfur-containing amino acids such as L-cystine can be consumed as additives to food to increase nutrition. They also play an important role in animal digestion, absorption, nutritional metabolism and immune function as well as other aspects.

Amino acids are commonly detected by methods such as high performance liquid chromatography (HPLC), high performance liquid chromatography-mass spectrometry (HPLC-MS), gas chromatography-mass spectrometry (GC-MS), capillary electrophoresis, and fluorescent probe detection method. At present, there are few reports about L-cystine detection around the world, where the detection is mainly carried out by chromatographic separation and analysis. For example, Xia Sujie et al. used HPLC with pre-column derivatization to determine L-cystine with a linear range of 0.02-1.00 mg/mL. Zhang et al. used HPLC to detect L-cystine with a linear range of 2-15 μM. Alwael et al. used reverse-phase liquid chromatography and mass spectrometry to detect L-cystine with a linear range of 0.25-250 μM.

However, these methods generally require a high cost (especially in expensive precision instruments), and complicated sample preparation procedures. Moreover, these methods are not available for online use or suitable for outdoor use. Therefore, there is an important trend in the research field to explore and develop a simple and fast method for amino acid analysis. Compared with other instrumental analysis methods, electrochemical methods have attracted increased attention due to their simplicity, sensitivity, and rapid results as well as other advantageous features. For example, cyclic voltammetry (CV), differential pulse voltammetry (DPV), and square wave voltammetry (SWV) have been used for detection of some amino acids.

Currently, reports of cystine detection with an electrochemical method mainly focus on amperometric sensors. Salimi el al. prepared a nickel-doped carbon ceramic electrode and used the CV method to detect L-cystine with a linear range of 1.0-450 μM and a detection limit of 0.64 μM. Zor el al. used a reduced graphene oxide/β-cyclodextrin composite membrane electrode to detect L-cystine with a linear range of 1.0-100 μM and a detection limit of 1.0 μM, and obtained binding constants of D-type and L-type cystine by combining DPV detection and model calculation. The issues with existing amperometric methods, in general, are inconvenient to carry and not available for online detection. Studies on cystine detection methods are still very limited around the world. Based on this, it is desirable to develop a simpler, faster, and more sensitive electrochemical method for detecting L-cystine.

Compared with amperometric sensors based on composite material-modified electrodes, potentiometric electrochemical sensors have advantages of light weight, easy preparation, and fast response, which are conducive to online and real-time monitoring and analysis of amino acids in actual samples. Potentiometric electrochemical sensors have been successfully applied to the determination of different amino acids, including L-histidine (L-His), L-cysteine (L-Cys), L-glutamic acid (L-Glu) and L-lysine (L-Lys). Moreover, an important development direction of potentiometric electrochemical sensing method is the combination of an ion-selective membrane with electrochemical characteristics and a field effect transistor (FET) based on a metal-dielectric-semiconductor device. Generally, FET devices with ion selection function are called ion-sensitive field effect transistors (ISFET). The ISFET devices have many advantages such as low cost, high sensitivity, fast response, easy miniaturization and integration, convenient use, and easy implementation of online monitoring. In recent years, the ISFET devices have been gradually adopted in the detection of biological molecules such as DNA, inosine, *Staphylococcus epidermidis*, and prions. However, there is no report on the potentiometric electrochemical sensing method to detect L-cystine yet.

SUMMARY

The present invention aims to overcome shortcomings of the prior art and provide a method and a sensor for detecting L-cystine.

In order to achieve the above objective, the present invention provides the following technical solutions:

A method for detecting L-cystine includes the following steps:

step (1): implanting a p-well in an N-type substrate on a Si substrate layer of an FET, constructing a source electrode and a drain electrode at the p-well by thermal evaporation and magnetron sputtering techniques, constructing a $SiO_2$ layer on the Si substrate layer provided with the p-well in the N-type substrate, the source electrode and the drain electrode, plating an Al—Cu alloy layer, a Cr—Pd alloy layer and an Au membrane layer sequentially on a substrate layer of a polysilicon gate electrode by the thermal evaporation and magnetron sputtering techniques, finally constructing a silicon nitride layer on the substrate layer of the polysilicon gate electrode and the $SiO_2$ layer, and extending the gate electrode by 0.1-500 mm to obtain a sodium 3,3'-dithiodipropane sulfonate (SPS) membrane-modified gold-gate electrode (GGE)/SPS;

step (2): preparing an ethanol solution of SPS, immersing a cleaned GGE of an extended gate FET (EGFET) in the ethanol solution of the SPS, allowing to stand still at 25° C., and then washing an immersed GGE to obtain a GGE/SPS;

step (3): connecting a reference electrode and the GGE/SPS to an electrode connector of the EGFET to form a differential amplifier circuit with two high-impedance ends, inserting the reference electrode and the GGE/SPS into a phosphate-buffered solution (PBS), connecting power connectors of the EGFET to positive and negative electrodes of a regulated power supply respectively, and connecting a signal output connector of the EGFET to a test port of a multimeter to form a complete sensing loop, where a potential change of a system can be sensitively detected based on FET in-situ signal amplification and a potential of the GGE/SPS as a working electrode in the PBS tends to stabilize gradually with time, when the potential is stable, adding test samples containing different concentrations of L-cystine to obtain corresponding potential response data to achieve detection of L-cystine in the test samples.

Preferably, in step (1), when plating the Al—Cu alloy layer, the Cr—Pd alloy layer and the Au membrane layer sequentially on the substrate layer of the polysilicon gate electrode by the thermal evaporation and magnetron sputtering techniques, a passivation is carried out with $Si_3N_4$. The Al—Cu alloy layer includes the following components in parts by weight: 40-68 parts of Al, 30-60 parts of Cu, 2-12 parts of Ni, 1-8 parts of Fe, 1-6 parts of Ti and 0.01-0.50 part of Nb; the Cr—Pd alloy layer includes the following components in parts by weight: 40-80 parts of Cr, 10-40 parts of Pd, 2-12 parts of Ni, 1-8 parts of Fe, 1-6 parts of Ti and 0.01-0.50 part of Nb; the Al—Cu alloy layer has a thickness of 20-600 nm, the Cr—Pd alloy layer has a thickness of 20-600 nm, and the Au membrane layer has a thickness of 20-1,000 nm.

Preferably, in step (2), the ethanol solution of the SPS has a concentration of 1.0-10.0 mmol/L. In step (2), the cleaned GGE of the EGFET is one cleaned with ultrapure water and absolute ethanol sequentially. In step (2), the cleaned GGE is immersed in the ethanol solution for 1-72 h. In step (2), the immersed GGE is washed with absolute ethanol and ultrapure water, then dried and stored.

Preferably, the reference electrode in step (3) is a saturated calomel electrode or an Ag/AgCl electrode arranged with a saturated KCl solution inside, and the working electrode is the GGE/SPS. In step (3), the PBS is has a pH of 3.0-8.0, preferably 5.0, and a concentration of 0.1 mol/L. The PBS is prepared by mixing and dissolving a predetermined amount of $NaH_2PO_4 \cdot 2H_2O$, $Na_2HPO_4 \cdot 12H_2O$ and NaCl in an appropriate ratio in water and adjusting the pH with 0.1 mol/L hydrochloric acid.

The present invention further provides a sensor for detecting L-cystine, including an FET, wherein a gate-extended gold electrode is arranged on the FET, namely, a gold-gate electrode (GGE), where in the gate-extended gold electrode, the gate is extended by 0.1-500 mm, and an SPS membrane is assembled on a surface of an Au membrane layer of the gold electrode.

The FET includes a Si substrate layer and a polysilicon gate electrode arranged on the Si substrate layer, wherein a p-well is implanted in an N-type substrate on the Si substrate layer, a source electrode and a drain electrode are arranged at the p-well, a $SiO_2$ layer is arranged on the Si substrate layer provided with the p-well in the N-type substrate, the source electrode and the drain electrode, an Al—Cu alloy layer, a Cr—Pd alloy layer and an Au membrane layer are sequentially plated on a substrate layer of the polysilicon gate electrode, and a silicon nitride layer is arranged on the substrate layer of the polysilicon gate electrode and the $SiO_2$ layer. The Al—Cu alloy layer has a thickness of 20-600 nm, the Cr—Pd alloy layer has a thickness of 20-600 nm, and the Au membrane layer has a thickness of 20-1,000 nm.

The sensor has an excellent Nernst response to the L-cystine with a linear range of $5.0 \times 10^{-6}$-$1.0 \times 10^{-3}$ mol/L, a response sensitivity of 58.25±1.5 mV/–pc (25° C.) and a detection limit of $2.69 \times 10^{-6}$ mol/L.

The present invention is further described below:

In the present invention, the GGE of FET is extended by a predetermined distance, for example, 0.1-500 mm, and SPS is self-assembled on the surface of the GGE to form a new sensor (GGE/SPS) for detecting L-cystine. Characterization by scanning electron microscope (SEM), electrochemical test and X-ray photoelectron spectroscopy (XPS) analysis of a sensing interface show that, the negatively charged SPS polyanion membrane in a solution adsorbs and binds the positively charged target L-cystine through electrostatic interaction, forming an electric double layer structure to generate a membrane potential identifying monovalent organic ammonium ions. The electrode has an excellent potential response to L-cystine in PBS (pH=5.0) with a linear range of $5.0 \times 10^{-6}$-$1.0 \times 10^{-3}$ mol/L, a response sensitivity of 58.25±1.5 mV/–pc (25° C.) and a detection limit of $2.69 \times 10^{-6}$ mol/L. The electrode has a fast response (30 s), excellent reproducibility and stability. Common amino acids such as L-glycine (L-Gly), L-alanine (L-Ala), L-valine (L-Val), L-aspartic acid (L-Asp), L-proline (L-Pro), L-threonine (L-Thr), L-His, L-leucine (L-Leu), L-tryptophan (L-Trp) and L-methionine (L-Met) do not interfere with the detection of L-cystine by the electrode. Moreover, the electrode can be used to detect L-cystine in actual pig serum samples with a recovery rate of 91.2-107.8%, indicating that the method of the present invention can be a simple and accurate new method for detecting L-cystine.

In summary, the present invention has developed a simple electrochemical sensor based on a selective membrane potential. The present invention also provides a new method for detecting L-cystine, that is, a method implemented by assembling SPS anion membrane on a surface of the Au membrane layer as an extended gate of FET, and using in-situ signal amplification of the FET to detect L-cystine sensitively. The sensor has an excellent Nernst response and can be used for rapid and sensitive detection of L-cystine in pig serum samples, thereby having potential application prospects in fields such as healthy breeding and life sciences.

DETAILED DESCRIPTION OF THE EMBODIMENTS

I. Experimental Process

1. Preparation of an Au Electrode with a SPS Self-Assembled Membrane 14.16 mg of SPS was taken and dissolved in 100 mL of ethanol to obtain a 4.0 mmol/L SPS/ethanol solution. An Au electrode was washed with ultrapure water and ethanol in sequence, then immersed in the SPS/ethanol solution, and allowed to stand still at 25° C. for 48 h. A modified Au electrode was taken out, washed with ethanol and ultrapure water, dried and stored to obtain the Au electrode with the SPS self-assembled membrane.

2. Design of an EGFET and Preparation of a GGE

Figure 1:
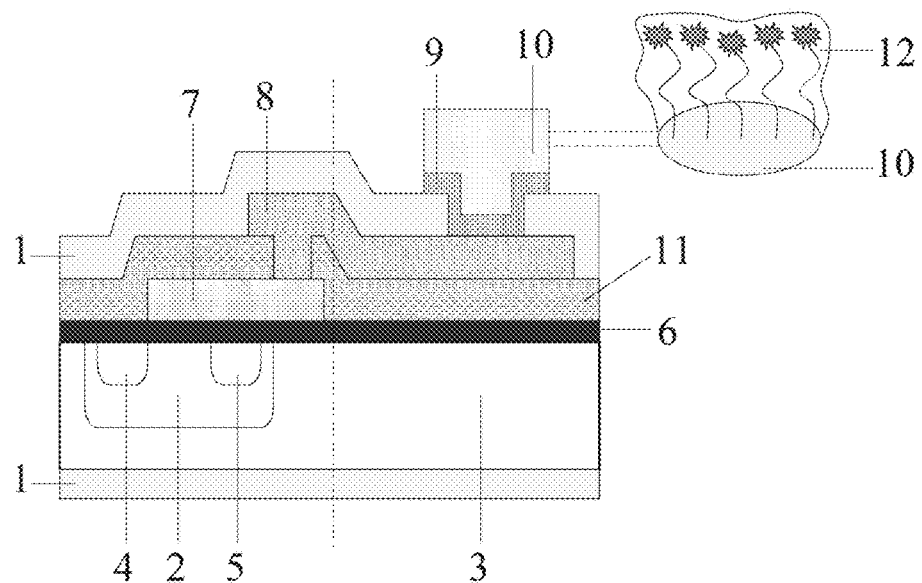
FIG. 1 is a schematic diagram showing a design of an EGFET with an extended gate; in the drawing: 1. Si substrate layer, 2. source electrode, 3. drain electrode, 4. p-well, 5. N-type substrate, 6. $SiO_2$ layer, 7. polysilicon gate electrode, 8. Al—Cu alloy layer, 9. Cr—Pd alloy layer, 10. Au membrane layer, 11. silicon nitride layer, 12. SPS membrane.

FIG. 1 is a schematic diagram showing a design of an FET with an extended gate. That is, based on a basic structure of metal-oxide-semiconductor field-effect transistor (MOS-FET), the p-well 2 was implanted in the N-type substrate 3 on the Si substrate layer 1 of the FET. Then the source electrode 4 and the drain electrode 5 were constructed at the p-well 2 by thermal evaporation and magnetron sputtering techniques. The $SiO_2$ layer 6 was constructed on the Si substrate layer 1 provided with the p-well 2 in the N-type substrate 3, the source electrode 4 and the drain electrode 5.

The Al—Cu alloy layer 8, the Cr—Pd alloy layer 9 and the Au membrane layer 10 were plated sequentially on the substrate layer of the polysilicon gate electrode 7 by the thermal evaporation and magnetron sputtering techniques. Finally, the silicon nitride layer 11 was constructed on the substrate layer of the polysilicon gate electrode 7 and the $SiO_2$ layer 6. The Al—Cu alloy layer 8 included the following components in parts by weight: 40-68 parts of Al, 30-60 parts of Cu, 2-12 parts of Ni, 1-8 parts of Fe, 1-6 parts of Ti and 0.01-0.50 part of Nb. The Cr—Pd alloy layer 9 included the following components in parts by weight: 40-80 parts of Cr, 10-40 parts of Pd, 2-12 parts of Ni, 1-8 parts of Fe, 1-6 parts of Ti, and 0.01-0.50 part of Nb. The Al—Cu alloy layer 8 had a thickness of 20-600 nm, the Cr—Pd alloy layer 9 had a thickness of 20-600 nm, and the Au membrane layer 10 had a thickness of 20-1,000 nm. The gate of the Au electrode was extended by 200 mm. An FET wafer was passivated with $SiO_2$ and $Si_3N_4$ to prevent the wafer excluding Au from contacting a solution, so as to form the EGFET. A surface of the membrane of extended GGE of the EGFET was subjected to different physical/chemical modification treatments to form a sensitive membrane to detect targets to be tested sensitively. According to the above method, SPS polyanion was self-assembled on the surface of the GGE to obtain the SPS 12-modified GGE/SPS.

3. Test of the GGE with the Self-Assembled Membrane

A buffer system for an electrode potential test was PBS (0.1 mol/L) with pH 3.0-8.0. The PBS was prepared by mixing and dissolving a predetermined amount of $NaH_2PO_4 \cdot 2H_2O$, $Na_2HPO_4 \cdot 12H_2O$ and NaCl in an appropriate ratio in water and adjusting the pH with 0.1 mol/L hydrochloric acid.

A saturated calomel electrode and the GGE/SPS were connected to electrode connectors of the EGFET to form a differential amplifier circuit with two high-impedance ends. The electrode was inserted into the PBS. Power connectors of the EGFET were connected to positive and negative electrodes of a regulated power supply, respectively. A signal output connector of the EGFET was connected to a test port of a multimeter to form a complete sensing loop. Potential changes of a system can be sensitively detected based on FET in-situ signal amplification. The potential of the GGE/SPS as a working electrode in the PBS stabilized gradually with time. When the potential was stable, test samples containing different concentrations of L-cystine were added to obtain corresponding potential response data to further obtain a standard curve. When testing an actual sample, a potential curve of the actual sample was compared with the standard curve to achieve the detection.

II. Experimental Results and Analysis

1. SEM Characterization of the GGE/SPS

Figure 2:
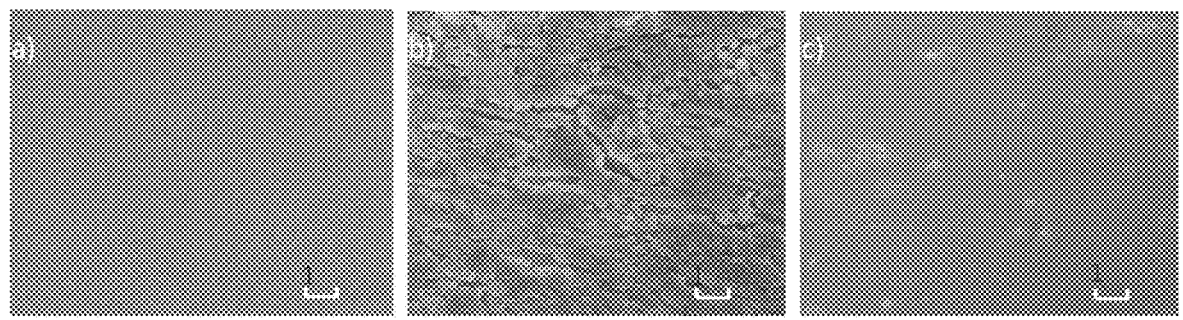
FIG. 2A is an SEM image of a surface of a bare Au electrode.
FIG. 2B is an SEM image of a surface of the electrode after SPS self-assembly.
FIG. 2C is an SEM image of a surface of the electrode after the detection of L-cystine.

Surface morphologies of the GGE/SPS before or after the detection of L-cystine were characterized by SEM images (as shown in FIG. 2A-C). FIG. 2A was an SEM image of a surface of a bare Au electrode. It can be seen that, the electrode surface was relatively flat and smooth. After SPS was self-assembled on the surface of the electrode (FIG. 2B), the surface of the electrode had a relatively dense and rough membrane, indicating that SPS formed a self-assembled membrane on the surface of the GGE. After detection of L-cystine by the electrode, numerous granular substances appeared on the surface (FIG. 2C). This structural change may be due to the combination of L-cystine and SPS by, for example, electrostatic adsorption. Relatively strong complex aggregation was formed, thereby changing the surface morphology of the electrode.

2. Response Mechanism and Electrochemical Characterization of the GGE/SPS

SPS was a substance which had a disulfide bond and a symmetrical structure with the disulfide bond as a center, where sulfur in the disulfide bond can form an Au—S bond with Au, thereby enabling self-assembly on the electrode surface. As a disulfide compound (RSSR), the SPS had the disulfide bond which was easily reduced and broken in an acidic electrolyte (0.1 mol/L PBS, pH=5.0) to form two identical structures with sulfhydryl groups. A reaction formula can be derived as follows:

$$R-S-S-R + 2H^+ + 2e^- \rightleftharpoons 2R-SH \tag{1}$$

Figure 3:
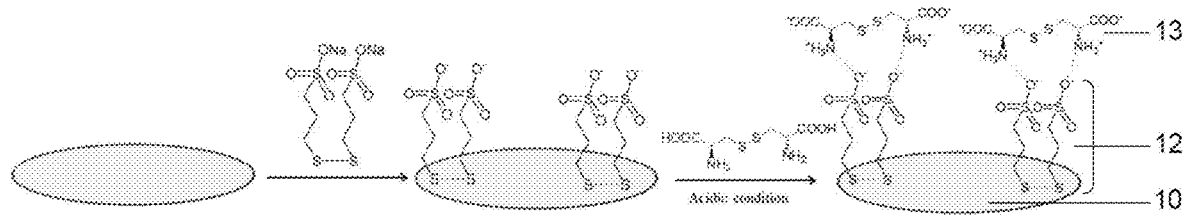
FIG. 3 is a schematic diagram showing a principle of recognition and responses of SPS molecules binding to L-cystine molecules, in the drawing: 10. Au membrane layer, 12. SPS membrane, 13. L-cystine.

Moreover, under acidic conditions, L-cystine was positively charged, while the end of the SPS containing a sulfonic group was negatively charged, attracting the positively charged amino group of L-cystine. Due to a steric hindrance structure, two sulfonic groups of the SPS molecule electrostatically adsorbed and bound to two positively charged amino groups of L-cystine. That is, one SPS molecule can bind to one L-cystine molecule. A schematic diagram of identification and response principle was shown in FIG. 3.

Figure 4:
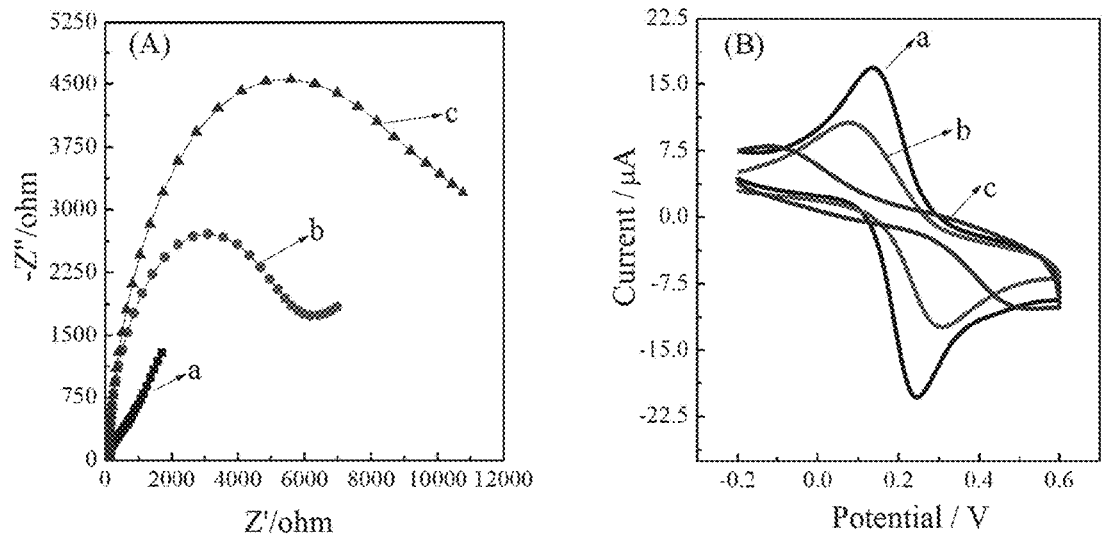
FIG. 4A is an alternating current (AC) impedance diagram of the electrode in a potassium ferricyanide solution (containing 2.0 mmol/L $K_3[Fe(CN)_6]$, 2.0 mmol/L $K_4[Fe(CN)_6]$ and 0.2 mol/L $Na_2SO_4$)
FIG. 4B is a cyclic voltammogram of the electrode in the potassium ferricyanide solution (containing 2.0 mmol/L $K_3[Fe(CN)_6]$, 2.0 mmol/L $K_4[Fe(CN)]$ and 0.2 mol/L $Na_2SO_4$); in the drawings: a. GGE, b. GGE/SPS, c. GGE/SPS/L-cystine.

In order to verify the interaction between the SPS carrier and the L-cystine, the present invention used AC impedance and CV methods to investigate electrochemical behaviors of the above electrodes with different modified membranes. Results were shown in FIG. 4A-B. FIG. 4A and FIG. 4B respectively show an AC impedance diagram and a cyclic voltammogram of the electrode in a potassium ferricyanide solution. In FIG. 4A, curve a represented a bare Au electrode with a small impedance value, and curve b represented an SPS-modified Au electrode. Compared with the bare Au electrode, the SPS-modified Au electrode had an obvious semicircle at high frequencies and a relatively large impedance. This indicated that SPS formed a relatively dense monomolecular self-assembled membrane layer on the Au surface through disulfide bonds, hindering electronic conduction of $[Fe(CN)_6]^{3-/4-}$ on the electrode surface. After binding to L-cystine ($1.0 \times 10^{-5}$ mol/L), the impedance value was greatly enhanced (as shown in curve c in FIG. 4A). This was due to the very strong adsorption and binding of SPS to L-cystine, which thickened the membrane layer on the surface of the Au electrode to greatly reduce electronic conductivity, thereby further increasing the impedance value of the electrode greatly. The change in the impedance value can be confirmed by corresponding electrochemical CV behaviors (as shown in FIG. 4B).

In FIG. 4B, curve a represented a bare Au electrode, which had an obvious oxidation peak and a reduction peak, indicating that the bare Au electrode after pretreatment had a strong ability to transfer electrons. In FIG. 48, curve b represented the SPS-modified Au electrode whose oxidation and reduction peaks were significantly smaller than those of the bare Au electrode. This indicated that SPS formed a non-conductive monomolecular self-assembled membrane layer on the Au surface through disulfide bonds, hindering electron conduction of $[Fe(CN)_6]^{3-/4-}$ on the electrode surface, and thereby resulting in a drop in peak currents. When the electrode was combined with L-cystine ($1.0 \times 10^{-5}$ mol/L), the oxidation and reduction peak currents were significantly reduced (as shown by curve c in FIG. 4B). This was due to the SPS-modified Au electrode adsorbing L-cystine, which reduced electronic conductivity, thereby reducing the electrochemical conduction currents.

This indicated that SPS adsorbed and bound L-cystine strongly. Therefore, the electrochemical behaviors of the electrode indicated that the sensing interface can be used for recognition and detection of L-cystine.

3. XPS Characterization of the GGE/SPS

Figure 5:
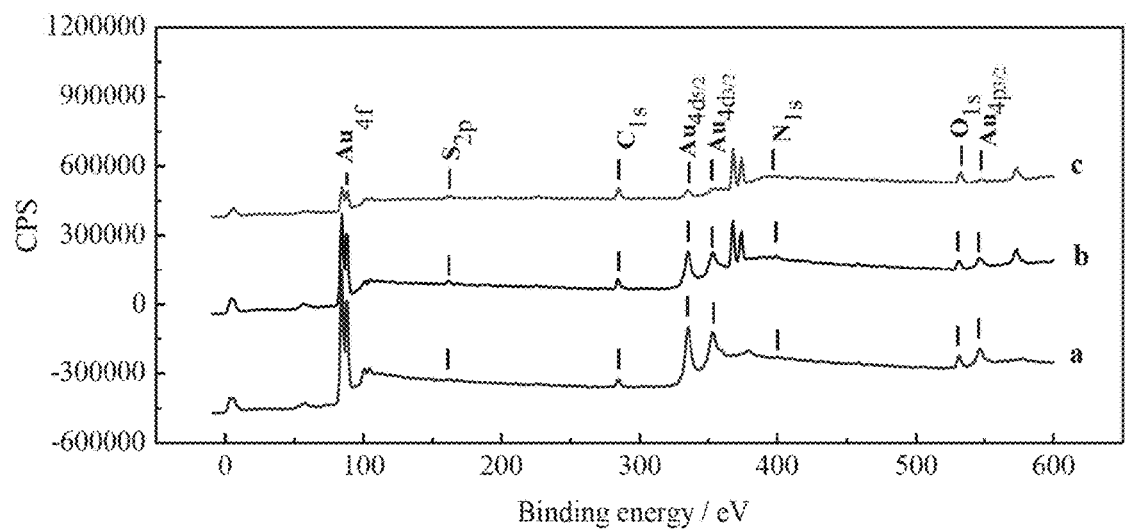
FIG. 5 is a diagram showing XPS full spectra of different electrode surfaces, in the drawing: a. GGE, b. GGE/SPS, c. GGE/SPS/L-cystine.

XPS was used to investigate identification of the target L-cystine by the electrode modified with a membrane. FIG. 5 showed XPS full spectra of the surfaces of the above different electrodes (GGE, GGE/SPS, and GGE/SPS/L-cystine). It can be seen from FIG. 5 that, compared with the bare Au electrode (curve a), the Au electrode after SPS self-assembly (curve b) had characteristic peaks of Au, $Au_{4f}$, $Au_{4d}$ and $Au_{4p}$, and also a characteristic sulfur peak $S_{2p}$ at the binding energy of 161.71 eV. This indicated that Au—S bonds were formed on the surface of the electrode, which proved that the SPS was successfully assembled on the surface of the Au electrode. Curve c represented the XPS spectrum of the surface of the GGE/SPS after identifying and binding L-cystine. From curves a, b, and c, it can be seen that the intensities of the three characteristic peaks of Au decreased substantially in the order of GGE>GGE/SPS>GGE/SPS/L-cystine. This may be due to the sequential combination of SPS and L-cystine on the electrode surface which caused greatly increased thickness of the surface, further proving that GGE/SPS firmly adsorbed and bound L-cystine molecules. From the binding energy data of different atoms in Table 1, it can be seen that the binding energy of $O_{1s}$ increased by 0.33 eV after binding to SPS, and decreased by 0.46 eV after further binding L-cystine. This was because in an acidic medium, the negatively charged sulfonic group of SPS had weak binding with $Na^+$ ($Na^+$ was released), so that oxygen exhibited a strong binding energy. When the SPS came into contact with L-cystine, there was strong electrostatic adsorption between the positively charged amino group of L-cystine and the sulfonic group of SPS, resulting in a decrease in the binding energy of O atom. Moreover, the Nis binding energy peak in curve c was slightly wider and larger than that in curve b. This indirectly proved that L-cystine was adsorbed on the electrode interface of the SPS, indicating that the sensing interface can identify L-cystine.

TABLE 1

Binding energies of different atoms

| | Au (eV) | S (eV) | O (eV) | N (eV) | C (eV) |
|---|---|---|---|---|---|
| GGE | 84.27 | — | 531.78 | 401.74 | 284.80 |
| GGE/SPS | 84.38 | 161.71 | 532.11 | 400.09 | 284.80 |
| GGE/SPS/L-cystine | 84.20 | 161.71 | 531.65 | 400.07 | 284.80 |

4. Selection of an Optimal pH

Figure 6:
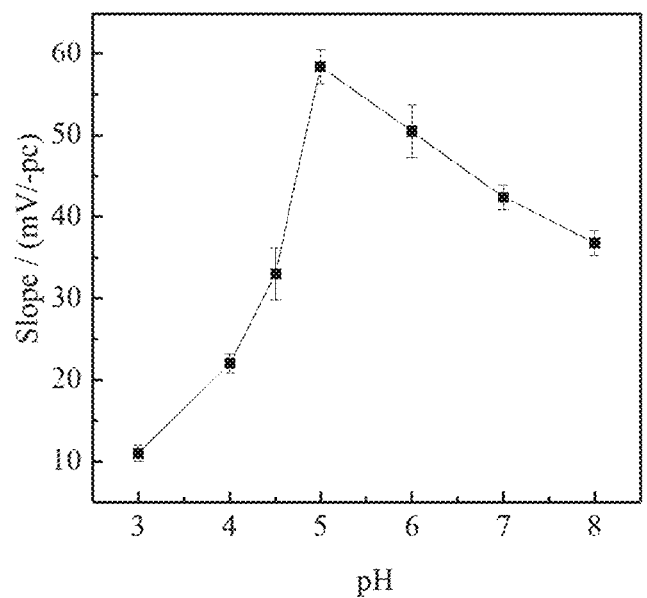
FIG. 6 is a diagram showing changes of slopes of the SPS membrane-modified GGE with pH (pH 3.0, 4.0, 4.5, 5.0, 6.0, 7.0, and 8.0)

The experiment investigated changes of potentials of the GGE electrode modified with the SPS membrane with concentrations of the L-cystine to be tested under different pH conditions (pH 3.0, 4.0, 4.5, 5.0, 6.0, 7.0, and 8.0), and based on this, calculated response slopes and drew a graph showing a relationship between the slopes and pH as shown in FIG. 6. It can be seen from FIG. 6 that, the electrode response slope was the largest at pH=5.0 (electrode response was the best), being 58.25±1.5 mV/-pc (25° C.), which was close to the theoretic Nernst response slope of positive monovalent ions. This showed that the overall charge contribution of L-cystine at pH=5.0 was equivalent to positive monovalent ions.

Figure 7:
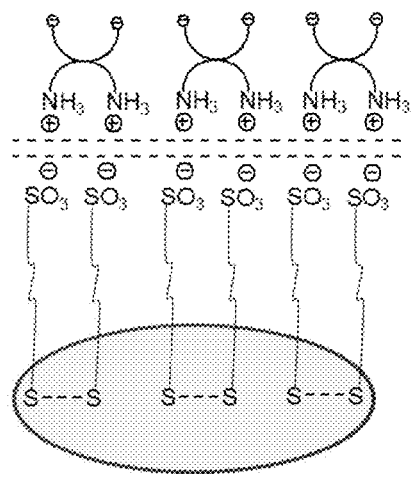
FIG. 7 is a schematic diagram showing a mechanism of responses and identification of potential ions.

Moreover, it can be further deduced that, in an acidic medium (pH=5.0), the sulfonic group of SPS was negatively charged and formed a negatively charged band of polyanion. In contrast, the amino group of L-cystine was positively charged and the carboxyl group of L-cystine had a very weak negative charge in the acidic medium. Due to strong electrostatic adsorption with the sulfonic group, the L-cystine showed molecular orientation movement to form a positive charged band of ammonium ion, thereby forming an electric double layer structure and generating a potential difference between phases for identifying and binding monovalent organic ammonium ions. A schematic diagram of the identification and responses mechanism of the potential ions was shown in FIG. 7.

5. GGE/SPS Response Performance

Figure 8:
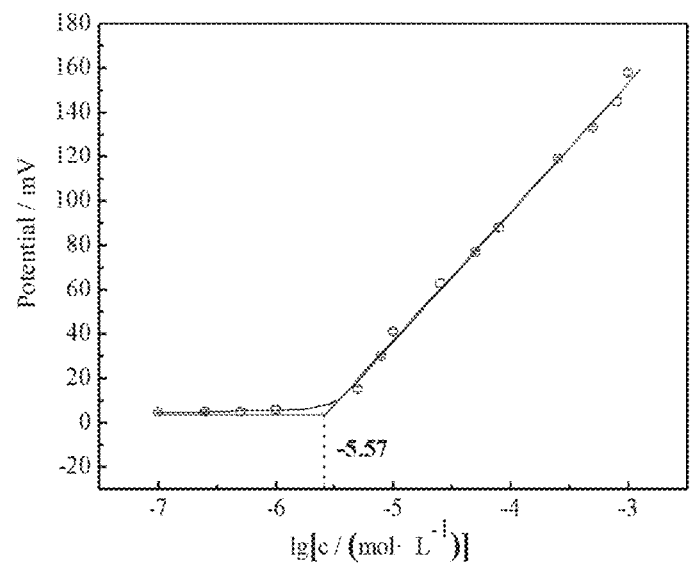
FIG. 8 is a diagram showing a curve of a potential response of the GGE/SPS in a PBS with pH=5.0 binding to different concentrations of L-cystine.

The experiment examined test response performance of the extended bare GGE and GGE/SPS to L-cystine. FIG. 8 was a curve showing a potential response of the GGE/SPS in a PBS with pH=5.0 binding to different concentrations of L-cystine. It can be seen from FIG. 8 that, as the concentration of L-cystine increased, the electrode potential gradually increased, indicating that there was increased number of L-cystine bonded on the surface of the GGE/SPS. Moreover, the electrode in a pH=5.0 PBS had a linear response to L-cystine within the range of $5.0 \times 10^{-6}$-$1.0 \times 10^{-3}$ mol/L. At the same time, a least squares method was used to obtain a linear response curve of electrode potential after fitting. A linear equation was $\Delta E = 328.6 + 58.25 \lg c$. Based on a graphic method, the electrode detection limit was $2.69 \times 10^{-6}$ mol/L (FIG. 8).

Figure 9:
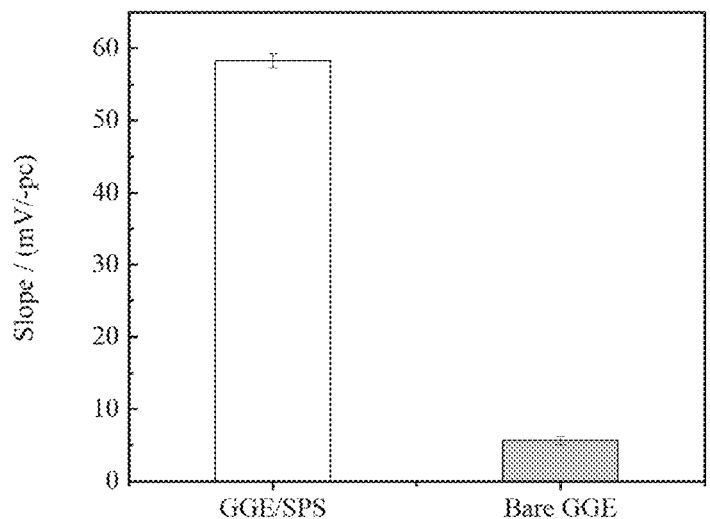
FIG. 9 is a histogram showing slopes of responses of a bare extended GGE and the GGE/SPS to L-cystine.

FIG. 9 was a histogram showing slopes of responses of a bare extended GGE and the GGE/SPS to L-cystine. It can be seen from FIG. 9 that, the potential of the bare GGE in response to L-cystine was very little or basically none. Therefore, SPS acted as a sensitive membrane, and it was feasible to have SPS modified on extended GGE to detect L-cystine.

Moreover, comparison of the GGE/SPS with L-cystine electrochemical sensors reported in other literatures (see Table 2) showed that, the GGE/SPS potentiometric sensor had a wider linear range and better selectivity than amperometric sensors. Furthermore, the GGE/SPS potentiometric sensor was simple to manufacture and operate, easy to achieve miniaturization and online monitoring.

The experiment also investigated reproducibility of the potential response of the prepared GGE/SPS to samples with different concentrations of L-cystine. That is, potential response values in alternating $1.000 \times 10^{-5}$ mol/L and $1.000 \times 10^{-4}$ mol/L of L-cystine sample solutions were measured with 10 measurements for each concentration. After statistical processing of data it was found that relative standard deviations of the potential response values of the electrode in two different concentration solutions were 2.43% and 0.85% respectively, which were relatively small. This indicated that the SPS membrane electrode had excellent reproducibility.

7. Selectivity of Electrode

Figure 11:
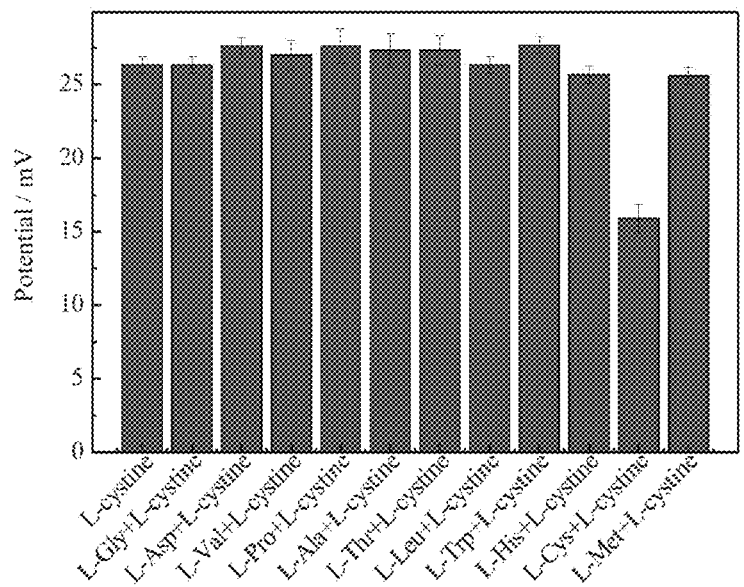
FIG. 11 is a diagram showing effects of common amino acids on detection of L-cystine by the GGE/SPS.

Effects of common amino acids on detection of L-cystine by the GGE/SPS were investigated in PBS with pH=5.0 (FIG. 11). A solution mixing method was used to keep the concentration of L-cystine to $1.000 \times 10^{-5}$ mol/L. Interference components such as common amino acids were added 50 times the concentration of L-cystine, where the concentration of L-Cys was $1.000 \times 10^{-5}$ mol/L.

Results showed that, after addition of L-Gly, L-Ala, L-Val, L-Asp, L-Pro, L-Thr, L-His, L-Leu, L-Trp and L-Met, the potential value of SPS membrane electrode in response to L-cystine hardly changed (FIG. 11), in other words, the interference was very small, while L-Cys had certain influence.

TABLE 2

Performance comparison of different electrodes

| Sensor electrode | Electrochemical method | Linear range (µmol/L) | Actual detection limit (µmol/L) | Selectivity | Applicability |
|---|---|---|---|---|---|
| Ni-CCE | Amperometric | 1.0-450 | 1.0 | \ | Poor stability, difficult to detect online |
| rGO/β-CD/GCE | Amperometric | 1.0-100 | 1.0 | \ | Poor stability, difficult to detect online |
| GGE/SPS | Potentiometric | 5.0-1,000 | 2.7 | Excellent | Excellent stability, long service life, suitable for online detection |

Note:
Ni-CCE: nickel-doped carbon ceramic electrode; β-CD: β-cyclodextrin; GCE: glassy carbon electrode; GGE: gold-gate electrode; rGO: reduced graphene oxide; SPS: sodium 3,3′-dithiodipropane sulfonate.

6. Determination of Response Time, Stability and Reproducibility

Figure 10:
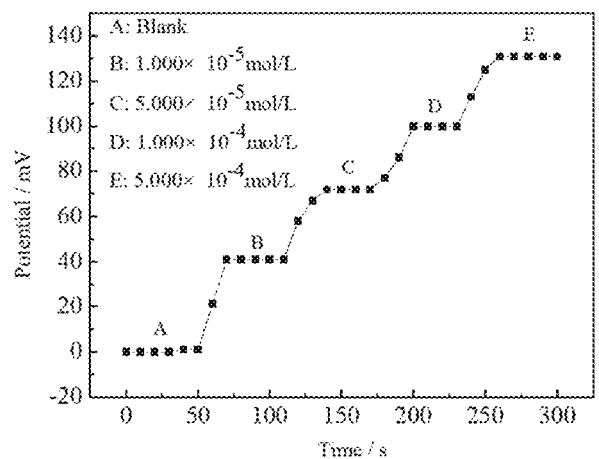
FIG. 10 is a diagram showing a time-potential response of the electrode after adding different concentrations of L-cystine to the PBS.

The experiment investigated response time and stability of the extended GGE/SPS in detection of L-cystine. FIG. 10 was a graph of a time-potential response of the electrode after adding different concentrations of L-cystine to the PBS. Determination of potential changing with time was carried out continuously from low to high concentrations in the range of $1.0 \times 10^{-5}$-$5.0 \times 10^{-4}$ mol/L. It can be seen that the time for reaction of the electrode to reach equilibrium over the entire concentration range was very short, being about 30 s when reaching 95% of the maximum potential response. Meanwhile, the electrode was used to test L-cystine samples for continuous 14 d, and its response slope changed to 41.55 mV/-pc, which was a decrease of 28.67%. This indicated that the membrane electrode can be used for more than 2 weeks with excellent stability and relatively long service life.

8. Determination of Recovery Rate and Analysis of Application

Under optimized experimental conditions, the extended GGE/SPS was used to determine L-cystine in actual pig serum samples. Prepared pig serum samples (taken from 6 live ternary hybrid piglets, weighing 7-15 Kg, provided by the Institute of Subtropical Agriculture, Chinese Academy of Sciences) were taken, diluted 10 times with pH5.0 PBS, and added with a known concentration of L-cystine. Determination was carried out by a standard addition method, and a recovery rate of L-cystine in the pig serum samples was 91.2-107.8% (see Table 3). This indicated that, the GGE/SPS enabled excellent accuracy, and thus can be used for rapid and sensitive detection of L-cystine in actual pig serum samples, showing potential applications in fields such as life medical and animal breeding.

TABLE 3

Determination of L-cystine content in pig serum samples by GGE/SPS and recovery rate

| Pig serum sample | Addition amount (μmol/L) | Measured value (μmol/L) | Relative standard deviation (%) | Recovery rate (%) |
|---|---|---|---|---|
| 1 | 4.000 | 4.310 | 3.680 | 107.8 |
| 2 | 6.000 | 6.210 | 2.270 | 103.5 |
| 3 | 8.000 | 8.600 | 1.730 | 107.5 |
| 4 | 10.00 | 9.120 | 1.630 | 91.20 |
| 5 | 12.00 | 11.89 | 1.400 | 99.08 |
| 6 | 14.00 | 14.90 | 1.210 | 106.4 |

In summary, the GGE/SPS of the present invention shows a sensitive Nernst response to L-cystine in PBS (pH=5.0) solution, with a linear response range of $5.00 \times 10^{-6}$–$1.0 \times 10^{-3}$ mol/L and a detection limit of $2.69 \times 10^{-6}$ mol/L. The electrode has a short response time (30 s) and excellent selectivity, reproducibility and stability and other features. Moreover, the electrode can be directly used to determine L-cystine in actual pig serum samples, and is expected to become a new online testing method for L-cystine.

What is claimed is:

1. A method for detecting L-cystine, comprising steps:
step (1): implanting a p-well in an N-type substrate, wherein the N-type substrate is arranged on a Si substrate layer of a field effect transistor (FET), constructing a source electrode and a drain electrode at the p-well by thermal evaporation and magnetron sputtering techniques to obtain a processed Si substrate layer, wherein the processed Si substrate layer is provided with the p-well in the N-type substrate, the source electrode and the source electrode, constructing a SiO2 layer on the processed Si substrate layer, plating an Al—Cu alloy layer, a Cr—Pd alloy layer and an Au membrane layer sequentially on a substrate layer of a polysilicon gate electrode by the thermal evaporation and magnetron sputtering techniques, finally constructing a silicon nitride layer on the substrate layer of the polysilicon gate electrode and the SiO2 layer, and extending the polysilicon gate electrode by 0.1-500 mm to obtain an extended gate FET (EGFET) with a gold-gate electrode (GGE);
step (2): preparing an ethanol solution of sodium 3,3'-dithiodipropane sulfonate (SPS), immersing a cleaned GGE of the EGFET in the ethanol solution of the SPS, allowing to stand still at 25° C. to obtain an immersed GGE, and then washing the immersed GGE to obtain an SPS membrane-modified GGE/SPS; and
step (3): connecting a reference electrode and the SPS membrane-modified GGE/SPS to an electrode connector of the EGFET to form a differential amplifier circuit with two high-impedance ends; inserting the reference electrode and the SPS membrane-modified GGE/SPS into a phosphate-buffered solution (PBS); connecting power connectors of the EGFET to a positive electrode and a negative electrode of a regulated power supply respectively, and connecting a signal output connector of the EGFET to a test port of a multimeter to form a sensing loop; wherein a potential change of the sensing loop is sensitively detected based on an FET in-situ signal amplification; a potential of the SPS membrane-modified GGE/SPS in the PBS tends to stabilize gradually with time, and the SPS membrane-modified GGE/SPS is used as a working electrode; when the potential of the SPS membrane-modified GGE/SPS is stable, adding test samples containing different concentrations of the L-cystine to obtain corresponding potential response data to achieve detection of the L-cystine in the test samples.

2. The method according to claim 1, wherein in step (1), when plating the Al—Cu alloy layer, the Cr—Pd alloy layer and the Au membrane layer sequentially on the substrate layer of the polysilicon gate electrode by the thermal evaporation and magnetron sputtering techniques, a passivation is carried out with $Si_3N_4$, the Al—Cu alloy layer comprises the following components in parts by weight: 40-68 parts of Al, 30-60 parts of Cu, 2-12 parts of Ni, 1-8 parts of Fe, 1-6 parts of Ti and 0.01-0.50 part of Nb, the Cr—Pd alloy layer comprises the following components in parts by weight: 40-80 parts of Cr, 10-40 parts of Pd, 2-12 parts of Ni, 1-8 parts of Fe, 1-6 parts of Ti, 0.01-0.50 part of Nb, the Al—Cu alloy layer has a thickness of 20-600 nm, the Cr—Pd alloy layer has a thickness of 20-600 nm, and the Au membrane layer has a thickness of 20-1,000 nm.

3. The method according to claim 1, wherein in step (2), the ethanol solution of the SPS has a concentration of 1.0-10.0 mmol/L.

4. The method according to claim 1, wherein in step (2), the cleaned GGE is immersed in the ethanol solution of the SPS for 1-72 h.

5. The method according to claim 1, wherein the reference electrode in step (3) is a saturated calomel electrode or an Ag/AgCl electrode arranged with a saturated KCl solution inside, and the working electrode is the SPS membrane-modified GGE/SPS.

6. The method according to claim 1, wherein in step (3), the PBS has a pH of 3.0-8.0 and a concentration of 0.1 mol/L.

7. A sensor for detecting L-cystine, comprising an FET, wherein a gate-extended gold electrode is arranged on the FET; a gate in the gate-extended gold electrode is extended by 0.1-500 mm, and a sodium 3,3'-dithiodipropane sulfonate (SPS) membrane is assembled on a surface of an Au membrane layer of the gate-extended gold electrode.

8. The sensor according to claim 7, wherein the FET comprises a Si substrate layer and a polysilicon gate electrode, and the polysilicon gate electrode is arranged on the Si substrate layer; a p-well is implanted in an N-type substrate and the N-type substrate is arranged on the Si substrate layer; a source electrode and a drain electrode are arranged at the p-well to obtain a processed Si substrate layer, wherein the processed Si substrate layer is provided with the p-well in the N-type substrate, the source electrode and the source electrode, a SiO2 layer is arranged on the processed Si substrate layer; an Al—Cu alloy layer, a Cr—Pd alloy layer and an Au membrane layer are sequentially plated on a substrate layer of the polysilicon gate electrode; and a silicon nitride layer is arranged on the substrate layer of the polysilicon gate electrode and the SiO2 layer.

9. The sensor according to claim 8, wherein the Al—Cu alloy layer has a thickness of 20-600 nm, the Cr—Pd alloy layer has a thickness of 20-600 nm, and the Au membrane layer has a thickness of 20-1,000 nm.

10. The sensor according to claim 7, wherein the sensor has a Nernst response to the L-cystine, and the sensor has a linear range of $5.0 \times 10^{-6}$–$1.0 \times 10^{-3}$ mol/L, a response sensitivity of $58.25 \pm 1.5$ mV/–pc (25° C.) and a detection limit of $2.69 \times 10^{-6}$ mol/L.

11. The sensor according to claim 8, wherein the sensor has a Nernst response to the L-cystine, and the sensor has a linear range of $5.0\times10^{-6}$-$1.0\times10^{-3}$ mol/L, a response sensitivity of $58.25\pm1.5$ mV/-pc (25° C.) and a detection limit of $2.69\times10^{-6}$ mol/L.

12. The sensor according to claim 9, wherein the sensor has a Nernst response to the L-cystine, and the sensor has a linear range of $5.0\times10^{-6}$-$1.0\times10^{-3}$ mol/L, a response sensitivity of $58.25\pm1.5$ mV/-pc (25° C.) and a detection limit of $2.69\times10^{-6}$ mol/L.

* * * * *